(12) United States Patent
De Franciscis et al.

(10) Patent No.: US 11,274,308 B2
(45) Date of Patent: Mar. 15, 2022

(54) ICAM-1 APTAMERS, DIAGNOSTIC AND THERAPEUTIC USES THEREOF

(71) Applicant: BRACCO IMAGING S.P.A., Milan (IT)

(72) Inventors: Vittorio De Franciscis, Naples (IT); Silvia Catuogno, Naples (IT); Carla Lucia Esposito, Naples (IT); Alessandro Maiocchi, Monza (IT); Margherita Iaboni, Qualiano (IT); Luisa Poggi, Banchette d'Ivrea (IT); Erika Reitano, Banchette (IT)

(73) Assignee: BRACCO IMAGING S.P.A., Milan (IT)

( * ) Notice: Subject to any disclaimer, the term of this patent is extended or adjusted under 35 U.S.C. 154(b) by 0 days.

(21) Appl. No.: 17/262,835

(22) PCT Filed: Jul. 24, 2019

(86) PCT No.: PCT/EP2019/069917
§ 371 (c)(1),
(2) Date: Jan. 25, 2021

(87) PCT Pub. No.: WO2020/020947
PCT Pub. Date: Jan. 30, 2020

(65) Prior Publication Data
US 2021/0292762 A1    Sep. 23, 2021

(30) Foreign Application Priority Data
Jul. 26, 2018 (EP) .................................. 18185794

(51) Int. Cl.
*C12N 15/115* (2010.01)
*C12Q 1/68* (2018.01)

(52) U.S. Cl.
CPC ........ *C12N 15/115* (2013.01); *C12N 2310/16* (2013.01); *C12N 2310/322* (2013.01); *C12N 2320/10* (2013.01); *C12N 2320/34* (2013.01)

(58) Field of Classification Search
None
See application file for complete search history.

(56) References Cited

U.S. PATENT DOCUMENTS 5,756,291 A    5/1998    Griffin et al.

FOREIGN PATENT DOCUMENTS

| WO | 2005110489 A2 | 11/2005 |
|---|---|---|
| WO | 2010144295 A1 | 12/2010 |
| WO | 2014068408 A2 | 5/2014 |
| WO | 2015031694 A2 | 3/2015 |

OTHER PUBLICATIONS

Almenar-Queralt, A. et al., "Apical topography and modulation of ICAM-1 expression on activated endothelium," Am. J. Pathol., 147:1278-1288 (1995).
Catuogno, S. et al., "Developing aptamers by cell-based SELEX," In: Nucleic Acid Aptamers: Selection, Characterization, and Application, Methods in Molecular Biology, 1380:33-46 (2016).
Ellington, A.D., et al., "In vitro selection of RNA molecules that bind specific ligands," Nature, 346:818-822 (1990).
Gao, S. et al., "Post-SELEX optimization of aptamers," Anal. Bioanal. Chem., 408:4567-4573 (2016).
Gopinath S.C. et al., "An RNA aptamer that distinguishes between closely related human influenza viruses and inhibits haemagglutinin-mediated membrane fusion," J. Gen. Virology, 87:479-487 (2006).
Hubbard, AK et al., "Intercellular adhesion molecule-1 (ICAM-1) expression and cell signaling cascades," Free Radical Biol. Med., 28:1379-1386 (2000).
International Search Report and Written Opinion for PCT/EP2019/069917, dated Oct. 29, 2019.
Koning et al., "Endothelial cells at inflammatory sites as target for therapeutic intervention," Endothelium, 9:161-171 (2002).
Levy-Nissenbaum, E. et al., "Nanotechnology and aptamers: applications in drug delivery," Trend Biotechnology, 26(8): 442-449 (2008).
Lupold, et al., "Identification and characterization of nuclease-stabilized RNA molecules that bind human prostate cancer cells via the prostate-specific membrane antigen," Cancer Res., 62:4029-4033 (2002).
Muro, et al., "Targeting of antioxidant and anti-thrombotic drugs to endothelial cell adhesion molecules," Curr.Pharm. Des., 11:2383-2401(2005).
Radom, F. et al., "Aptamers: Molecules of great potential," Biotechnol. Adv., 31:1260-1274 (2013).
Song, K.M. et al, "Aptamers and their biological applications," Sensors, 12:612-631 (2012).
Stoltenburg, R. et al., "SELEX-A (r)evolutionary method to generate high-affinity nucleic acid ligands," Biomol. Eng., 24:381-403 (2007).
Tuerk, C. et al., "Systematic evolution of ligands by exponential enrichment: RNA ligands to bacteriophage t4 DNA polymerase," Science, 249:505-510 (1990).

*Primary Examiner* — Sean McGarry
(74) *Attorney, Agent, or Firm* — Vivicar Law, PLLC

(57) ABSTRACT

The present invention provides nucleic acid aptamers binding to the Intercellular Adhesion Molecule-1 (ICAM-1), derivatives and conjugates thereof and their use as diagnostic tools, particularly for the imaging of organs and tissues expressing ICAM-1, or as therapeutic agents for prevention or treatment of ICAM-1-related diseases.

14 Claims, 11 Drawing Sheets
Specification includes a Sequence Listing.

ICAM-1 APTAMERS, DIAGNOSTIC AND THERAPEUTIC USES THEREOF

CROSS-REFERENCE TO RELATED APPLICATIONS

This application is the national stage application of corresponding international application number PCT/EP2019/069917, filed Jul. 24, 2019, which claims priority to and the benefit of European application no. 18185794.7, filed Jul. 26, 2018, which is hereby incorporated by reference in its entirety.

BACKGROUND OF THE INVENTION

The present invention provides nucleic acid aptamers binding to the Intercellular Adhesion Molecule-1 (ICAM-1), derivatives and conjugates thereof and their use as diagnostic tools, particularly for the imaging of organs and tissues expressing ICAM-1, or as therapeutic agents for prevention or treatment of ICAM-1-related diseases.

Aptamers

Recently, functional oligonucleotide-based biomolecules, called aptamers, have attracted great interest as potential alternatives to antibodies. The technology of aptamer selection has been drawn to the attention of the scientific community due to its applicability in diagnosis and treatment of diseases.

The oligonucleotide aptamers range in size from about 20 to about 80 bases (8 to 25 kDa) and their structures are responsible for intramolecular interactions (Levy-Nissenbaum E. et al., *Trends Biotechnol.* 2008, 26(8), 442-449).

Aptamers bind to their targets by interactions between aromatic compounds, base pairings by hydrogen ligation, van der Waals interactions, and electrostatic interactions between charged groups or hydrogen bonds. In consequence, aptamers undergo conformational changes after target recognition and biomolecular interaction.

These biological, physical and chemical properties make these oligonucleotides effective recognition tools for diagnosis and therapy. The application of aptamers in biological fields is mainly limited due to its degradation by ribozymes. Chemical modifications are required in order to protect them against nucleases, improving their thermal stability and their pharmacokinetic properties.

Among the modifications, the exchange of an OH at the 2'-position of the ribose by 2'-F or 2'-$NH_2$ can be performed to improve aptamer stability in the cellular environment. Other alterations of aptamers can include terminal capping with small molecules such as amine, a phosphate group, or residue of thymidine and other non-natural bases (Gao S. et al, *Anal. Bioanal. Chem.* 2016, 408(17), 4567-4573).

The aptamers are selected by an in vitro process through the Systematic Evolution of Binding by Exponential Enrichment (SELEX). This method was concomitantly described by Tuerk and Gold (*Science,* 1990, 249, 505-510) and Ellington and Szostak (*Nature,* 1990, 346, 818-822). SELEX involves the progressive selection of aptamers by the repetition of binding cycles, elution, and amplification of ligands from a random nucleic acid library, to select sequences with a higher binding affinity for the target.

A new application of this technology, called "cell-SELEX" has been developed allowing the selection of aptamers that bind to specific target cells (de Franciscis V. et al., *Methods Mol Biol.,* 2016, 1380, 33-46).

The selection parameters can be easily manipulated to obtain more efficient aptamers for a wide range of conditions (pH, temperature or buffer composition) (Radom F. et al, *Biotechnol. Adv.* 2013, 31(8), 1260-1274). Some modifications have been included in the traditional SELEX method, such as affinity chromatography, capillary electrophoresis and filtration membranes to maximize affinity and specificity and to improve the selection speed and success rate of the selected aptamers (Stoltenburg R et al, *Biomol. Eng.* 2007, 24(4), 381-403). The characteristics of the selected oligonucleotides are identified using various physical, chemical and biological assays (Song K M et al, *Sensors,* 2012, 12(1), 612-631).

Once selected, they can be synthesized in great quantity with precision and reproducibility by chemical reactions. These chemical processes are more cost-effective than the production of antibodies. When compared to antibodies, the aptamers have a relatively small size, which facilitates their chemical synthesis and possible modifications. They are biocompatible and poorly immunogenic in vivo. They have high selectivity and the ability to bind and recognize specific targets, presenting an affinity constant (Kd) with nanomolar range, compared to antibodies (Kd in the milli/micromolar range). Also, they penetrate tissues faster and more efficiently because of their significantly lower molecular weight and can distinguish extracellular or intracellular domains of proteins, which cannot be differentiated by antibodies (Gopinath S.C. et al, *J. Gen. Virol.,* 2006, 87(3), 479-487).

The strong target affinity/selectivity, cost-effectivity, chemical versatility and safety of aptamers are superior to traditional peptide- or protein-based ligands, which make them particularly suitable for molecular imaging. Therefore, aptamers are considered to be extremely useful to guide various imaging contrast agents to the target tissues or cells for optical, magnetic resonance, nuclear, computed tomography, ultrasound and multimodality imaging.

ICAM-1

Intercellular adhesion molecules (ICAMs) are structurally related transmembrane glycoproteins of the immunoglobulin supergene family and are ligands for the β2 integrin molecules present on leukocytes (Almenar-Queralt A. et al., *Am. J. Pathol.,* 1995, 147(5), 1278-1288; Hubbard A K et al, *Free Radic. Biol. Med.,* 2000, 28, 1379-1386). Of the five ICAMs identified, ICAM-1 is the most extensively studied (Koning et al., *Endothelium,* 2002, 9, 161-171; Muro et al., *Curr. Pharm. Des.,* 2005, 11, 2383-2401). ICAM-1 (Intercellular Adhesion Molecule 1) is a protein that in humans is encoded by the ICAM1 gene. This gene encodes a cell surface which is typically expressed on endothelial cells and cells o f the immune system. It binds to integrin o f type CD11a/CD18, or CD11b /CD18 and is also exploited by rhinovirus as a receptor.

ICAM-1 specifically participates in trafficking of inflammatory cells, in leukocyte effector functions, in adhesion of antigen-presenting cells to T lymphocytes, in microbial pathogenesis, and in signal transduction pathways through outside-in signaling events. This adhesion molecule is localized to both the apical and basolateral surface of endothelial cells, making it ideally positioned to facilitate transendothelial migration of leukocytes. In fact, ICAM-1 (along with VCAM-1) is considered to represent the most important adhesion molecule for leukocyte recruitment to inflamed sites and it is associated with a number of inflammatory and immune responses, as well as with epithelial tumorigenesis in the metastatic process. These properties makes ICAM-1 a potential target for diagnostic applications.

Non-invasive in vivo molecular imaging of endothelial ICAM-1 expression could therefore provide valuable insights in the progression of cardiovascular disease-related inflammation to improve diagnosis and treatment.

In recent years, contrast-enhanced ultrasonography (CEUS) has dramatically improved the imaging of small blood vessels. The microbubble-based contrast agents currently used in clinical practice lack affinity for the lesions, resulting in imaging duration only about 2-5 min. With the development of targeted ultrasound contrast agents and the appearance of nanobubbles, the ultrasound molecular imaging technique has undergone a revolutionary progress and become the focus of ultrasound applications. Also in this context the endothelial ICAM-1 is one of the most promising targets.

U.S. Pat. No. 5,756,291 discloses a method to obtain aptamers against target proteins such as ICAM-1, VCAM, Factor X, PDGF, FGF, E-selectin, thrombin and bradykinin. As far as ICAM-1 is concerned, the target is represented by five peptides from its amino terminus, from 17 to 19 residues in length, encompassing its active domain. The oligonucleotides mixture is radiolabeled with $^{32}$P, incubated with the target and then loaded on a gel. The pool enrichment is followed by gel shift method and selection of the best candidate. DNA species were selected for their slower migration compared to the starting pool. However, there is no evidence that the selected aptamer could bind ICAM-1 in the context of the cellular membrane, thus resulting a good tool for in vivo purposes.

WO2005/110489 discloses a method to increase the ligand antagonist range of a receptor-binding aptamer. The aptamer is joined to a high molecular weight steric group able to prevent the binding of the target to a second molecule. In the ICAM-1 context, the aptamer is directed against the domain 2 of the extracellular portion of the target, whereas the steric group prevents the binding of ICAM-1 natural ligand, the integrin LFA-1, to the domain 1. However, no sequences of aptamers with affinity for ICAM-1 are disclosed.

DESCRIPTION OF THE INVENTION

The present invention is based on the identification of RNA aptamers, which are able to bind ICAM-1 molecule with high affinity. In particular, the aptamers of the invention solve the problem of specifically recognize the target at the site where it is physiologically present, i.e. on the cell surface where ICAM-1 is expressed, thus demonstrating to be suitable for their use in vivo. In fact, the aptamers herein described have been found able to bind directly the cells overexpressing ICAM-1 on their surface.

To that purpose, a library of RNA molecules was assayed for its binding to COS7 cells transiently transfected with human ICAM-1. Following to repeated selection steps, the RNA molecules showing highest COS7-ICAM-1 binding were isolated and their sequence and ICAM-1 binding affinity were determined.

The aptamer having the following sequence:
UCAUGAUACGUUGCGUGAGCAACUGCGGCGCUAAAGUUUGGUUGACUAGUACAUG (SEQ ID NO: 1)
showed the highest binding affinity to ICAM-1.

Aptamers containing SEQ ID NO: 1 proved likewise able to bind ICAM-1 and particularly the aptamer having the following sequence:
GGGAAGAGAAGGACAUAUGAUCAUGAUACGUUGCGUGAGCAACUGCGGCGCUAAAGUUUGGUUGACUAGUACAUGACCACUUGA (SEQ ID NO: 2).

Therefore, in a first aspect the invention provides an aptamer able to bind to Intercellular Adhesion Molecule-1 (ICAM-1) and comprising the RNA sequence SEQ ID NO: 1.

In one embodiment, the above aptamer has a length of up to 100 nucleotides. The dissociation constants of the aptamers containing SEQ ID NO: 1 and showing ICAM-1 binding ability, determined by either RT-qPCR or flow-cytometry, were found within a range from 500 nM to 50 nM.

In a further aspect, the invention provides an aptamer able to bind to Intercellular Adhesion Molecule-1 (ICAM-1) and comprising the RNA sequence SEQ ID NO: 2.

In a preferred embodiment the RNA aptamers defined above are characterized by being nuclease-resistant.

In a more preferred embodiment the RNA aptamers defined above are characterized by having all the pyrimidine residues modified to 2'-fluoropyrimidines.

A preferred aptamer of the invention consists of SEQ ID NO: 2. More preferably, it consists of SEQ ID NO: 1.

Aptamers Modification

Aptamers of the invention can be modified, e.g. to increase their resistance to nucleases, to modulate their pharmacokinetics, or to be conjugated with diagnostic or therapeutic moieties.

Preferably, a RNA aptamer of the invention has at least one or all of the pyrimidine residues modified to 2'-fluoropyrimidines. Furthermore, its modification may include a chemical substitution at a sugar position, a chemical substitution at a phosphate position and a chemical substitution at a base position of the nucleic acid. In some embodiments, the modification is selected from the group consisting of: biotinylation, incorporation of a fluorescent label, incorporation of a modified nucleotide, 2'-pyrimidine modification, 3'-position capping, conjugation to a linker, conjugation to a compound or a drug, conjugation to a cytotoxic moiety, and labeling with a fluorophore, a radioisotope, an ultrasound contrast agent or a reporter moiety. The position of the modification can be varied depending on the type of moiety that is attached to the aptamer.

The aptamers of the invention, suitably labeled or conjugated with reporter or therapeutic moieties, can be used in the diagnosis, therapy or visualization of ICAM-1-related states, disorders, dysfunctions, conditions or diseases, particularly inflammation or inflammation-associated diseases. Exemplary applications include the diagnosis or therapy of: vascular inflammation in atherosclerosis and myocardial infarction; diseases affecting the cardiovascular system, such as myocarditis; inflammatory cardiomyopathy and heart failure.

In a particular embodiment of invention, the aptamers labeled with a reporter moiety are used in the imaging of body tissues or organ systems expressing ICAM-1 and particularly the endothelium and blood vasculature. Suitable imaging techniques include magnetic resonance imaging, positron-emission tomography (PET), computed tomography (CT), ultrasound, photoacoustic imaging (PAI), near-infrared fluorescence (NIRF), single photon emission computed tomography (SPECT).

For imaging applications, the reporter moiety linked to the aptamer is generally selected from: molecules capable of generating a fluorescent signal, such as fluorescein; FITC; Alexa dyes; Cy dyes; DyLight dyes; IRDye dyes or VivoTag dyes; optical moieties, including agents that may be used to produce contrast or signal using optical imaging; magnetic moieties, including a chelating agent for magnetic resonance agents which is able to form stable complexes with paramagnetic metal ions; radiolabel moieties; X-ray moieties that may be used to produce contrast or signal using X-ray imaging, such as iodinated organic molecules or chelates of heavy metal ions; ultrasound imaging moieties that may be used to produce contrast or signal using ultrasound targeted microbubbles; and photoacoustic imaging moieties, including photoacoustic imaging-compatible agents.

The aptamer and the reporter moiety or label may be linked either covalently or noncovalently, optionally by interposition of a suitable linker or spacer, including peptides, amino acids or nucleic acids. Furthermore, the aptamer and the reporter moiety or label may be linked using a tag system, including biotin/avidin, biotin/streptavidin, biotin/NeutrAvidin, or digoxigenin (DIG) systems.

In a further aspect, the invention provides a composition comprising an aptamer as herein defined. The ingredients of the composition can be varied depending on the intended use, whether for diagnostic, therapeutic or imaging applications. In particular the composition may contain a RNA molecule and one or more therapeutic compounds and/or one or more imaging agents.

In one embodiment, the composition is used for the imaging of a target tissue bearing ICAM-1 and comprises the aptamer conjugated or labeled with a reporter moiety as above defined. The composition can be e.g. in the form of a liposome or nanoparticles and it is suitable for parenteral administration, particularly for intravenous administration. Said composition can be used for visualizing ICAM-1 expressing tissues or organs, such as inflamed endothelium and vasculature.

Brief description of the Sequence Listing

```
sets out sequence from the 5' of the aptamer
10.T (55 nt)
                                          SEQ ID NO: 1
5'UCAUGAUACGUUGCGUGAGCAACUGCGGCGCUAAAGUUUGGUUGACU

AGUACAUG 3' sets out sequence from the 5' of the aptamer
12c-10 (84 nt)
                                          SEQ ID NO: 2
5'GGGAAGAGAAGGACAUAUGAUCAUGAUACGUUGCGUGAGCAACUGCG

GCGCUAAAGUUUGGUUGACUAGUACAUGACCACUUGA 3'
```

EXPERIMENTAL SECTION

Equipment

Flow cytometry data acquisition was performed using a BD Accuri™ C6 flow cytometer (BD Bioscience). RT-qPCR was carried out by StepOne™ Plus Real-Time PCR System (Applied Biosystems). Gel visualization was performed with Gel Doc EZ System (Bio-Rad). ELONA data were acquired by Multiskan™ FC Microplate Photometer (ThermoFisher Scientific).

List of Abbreviations

ICAM-1 Intercellular Adhesion Molecule-1
SELEX Systematic Evolution of Ligands by Exponential enrichment
RNA Ribonucleic acid
DNA Deoxyribonucleic acid
WT Wild type
nt nucleotides
HSA Human serum albumin
Kd Constant of dissociation
HMEC-1 Human mammary epithelial cells -1
TNFalpha Tumor necrosis factor alpha
COS7 CV-1 (simian) in Origin with SV40 genetic material cells
Rt-q PCR Real-time polymerase chain reaction

EXAMPLE 1

Selection of Anti-ICAM-1-Aptamers

To specifically select an aptamer for ICAM-1, a cell-SELEX approach was followed using the same cell line with and without the overexpressed target, instead of two cell lines (positive/negative) that differ also for other proteins present on the cell surface.

To this end, COS7 cells were transiently transfected with the expression plasmid pCMV6-ICAM-1.

Figure 1:
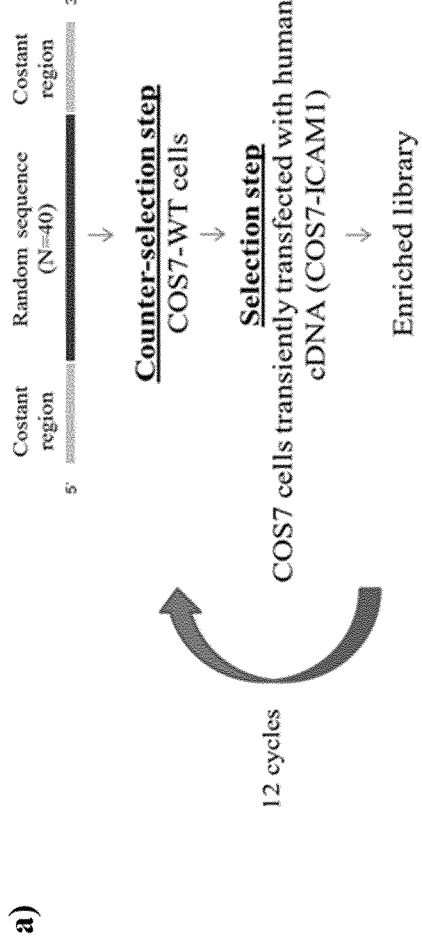
FIG. 1. Scheme of anti-ICAM-1 cell-SELEX procedure.
Figure 2:
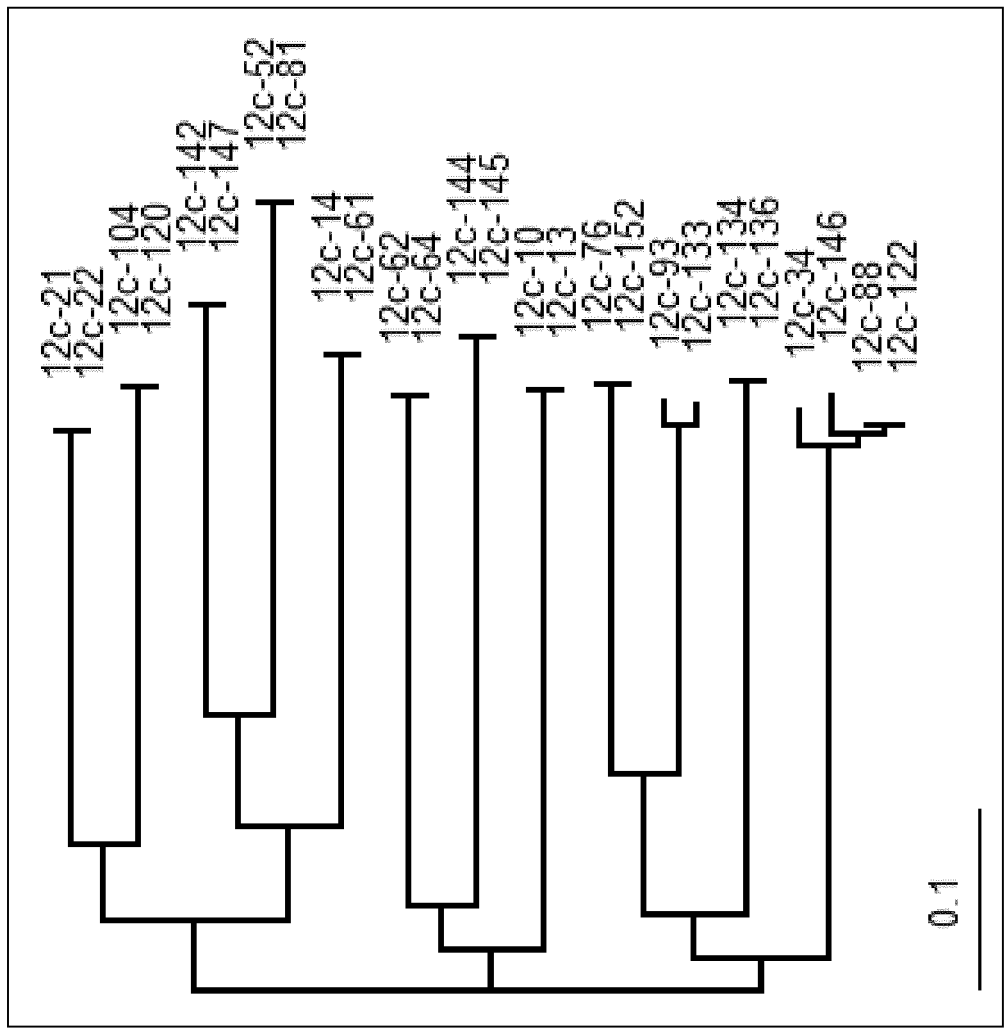
FIG. 2. Dendrogram (by MUSCLE algorithm) for the visualization of the enriched sequences obtained by cloning the last cycle of anti-ICAM-1 cell-SELEX.

In detail, to selectively target ICAM-1, a cell-SELEX protocol was performed transiently transfecting the human ICAM-1 cDNA in negative COS7 cells, used as a recipient cell line. The approach included 12 cycles of counter-selection/selection steps of a starting highly complex library on WT (COS7-WT) and transiently transfected COS7 cells (COS7-ICAM-1), respectively, according to the scheme in FIG. 1-a, in which at each round a selective pressure was generated (FIG. 1-b).

Before each round of cell-SELEX, the pool was transcribed using a mutant form of T7 RNA polymerase able to incorporate 2'-fluoro pyrimidines in the RNA sequences. At the end of cell-SELEX protocol, the last cycle was cloned and 164 samples were sequenced. Resulting sequences were analyzed for enrichment by alignment and a dendrogram was produced for the visualization of identical sequences or sequences with a single mismatch by MUSCLE algorithm.

Figure 3:
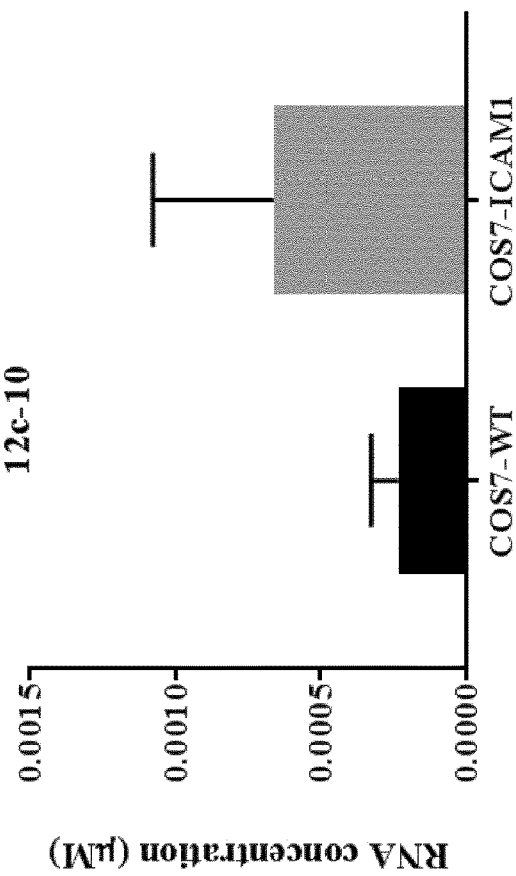
FIG. 3. RT-qPCR binding assay for the selected sequence by anti-ICAM-1 cell-SELEX. a) Experimental triplicates of the three sequences by RT-qPCR biding assay; b) Summary table of experimental triplicate fold change. Each bar shows the mean±standard deviation values from three experiments.
Figure 4:
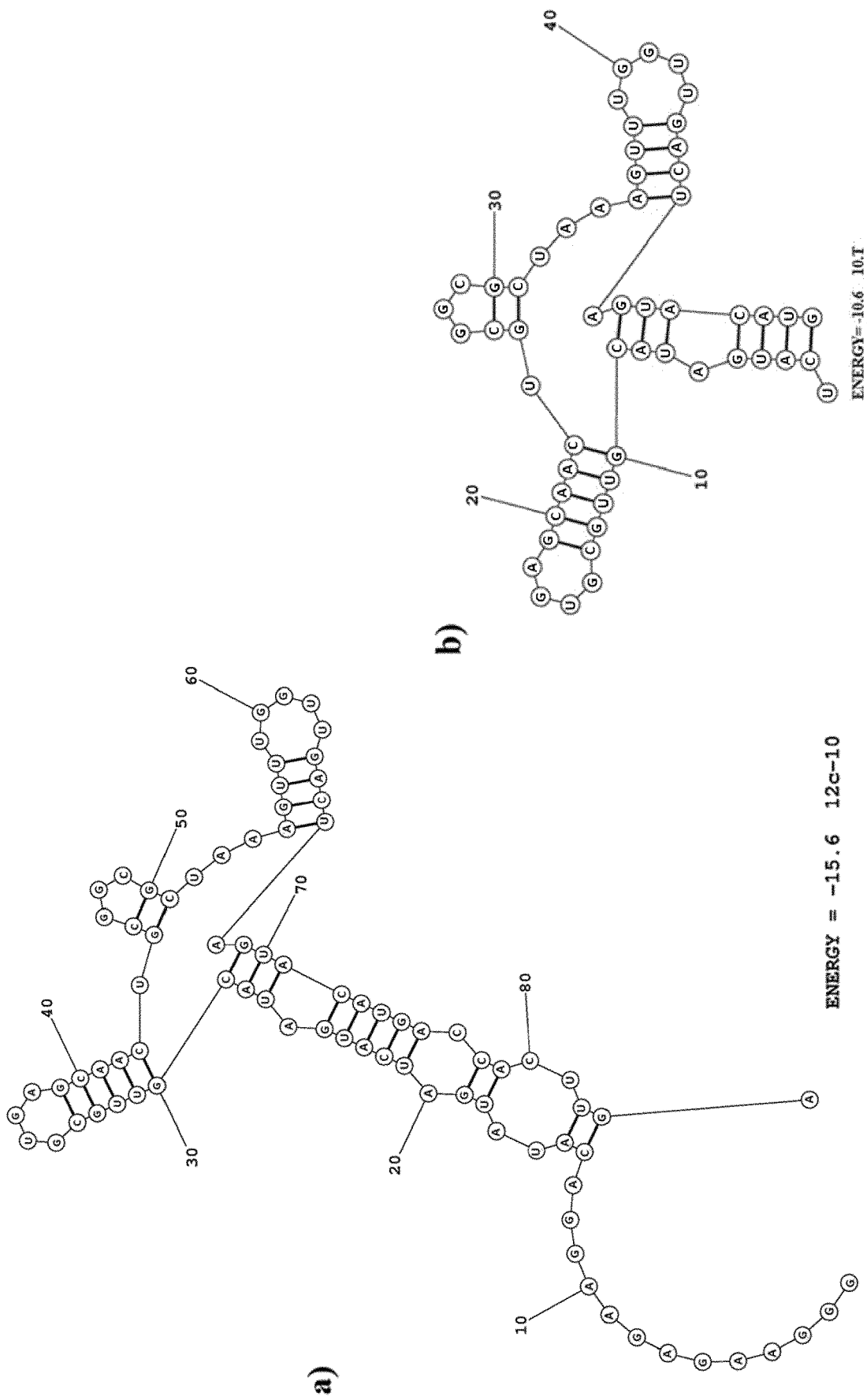
FIG. 4. Predicted secondary structure of the selected aptamer anti-ICAM-1 and relative shortened version by RNA structure 5.8 program. a) long 12c-10 sequence (SEQ ID NO: 2) and b) short 10.T sequence (SEQ ID NO: 1) predicted secondary structures with lower free energy.

Following the analysis of the enriched sequences, binding assays by RT-qPCR were performed in order to select the sequences able to bind COS7-ICAM-1. Essentially, DNA sequences were amplified and transcribed. Then, RNA sequences were incubated at 50 nM, as final concentration, for 15 minutes at 37° C., after pre-treatment with yeast tRNA 200 µg/mL, on COS7-WT and COS7-ICAM-1. Following incubation, cells were washed 3 times with PBS and recovered in TRIsure reagent. An RNA sequence used as reference control was spotted in each point for the normalization. A fold ratio was calculated comparing binding values of COS7-ICAM-1 over COS7-WT. Twelve sequences representatives of couples or groups of identical sequences were screened. Those with higher fold ratio were chosen for further analysis performing experimental triplicates. Results showed that 12c-10, consisting of SEQ ID NO: 2, confirmed the highest binding for COS7-ICAM-1 with respect to COS7-WT, as illustrated in FIG. 3 (the fold change, i.e. the ratio between binding value of COS7-ICAM-1 and binding value of COS7-WT, is 3.13).

In order to obtain a shorter sequence useful for imaging applications, the 84mer original molecule 12c-10, corresponding to SEQ ID NO: 2, was truncated to obtain the shorter 55mer sequence 10.T, corresponding to SEQ ID NO:1.

The sequence was shortened by isolating the more structured region (characterized by stems, loops, bulges and/or hairpins) including the degenerate portion of the starting library, taking into account that the folding of the short version has to be maintained.

EXAMPLE 2

Binding and Affinity of Aptamer 10.T to COS7-ICAM-1

To the aim of testing if the short aptamer 10.T (SEQ ID NO: 1) contained the active site of the original molecule 12c-10 (SEQ ID NO: 2) and preserved high binding and affinity to COS7-ICAM-1, binding assays were performed maintaining the same conditions used for long aptamers screening.

Figure 5:
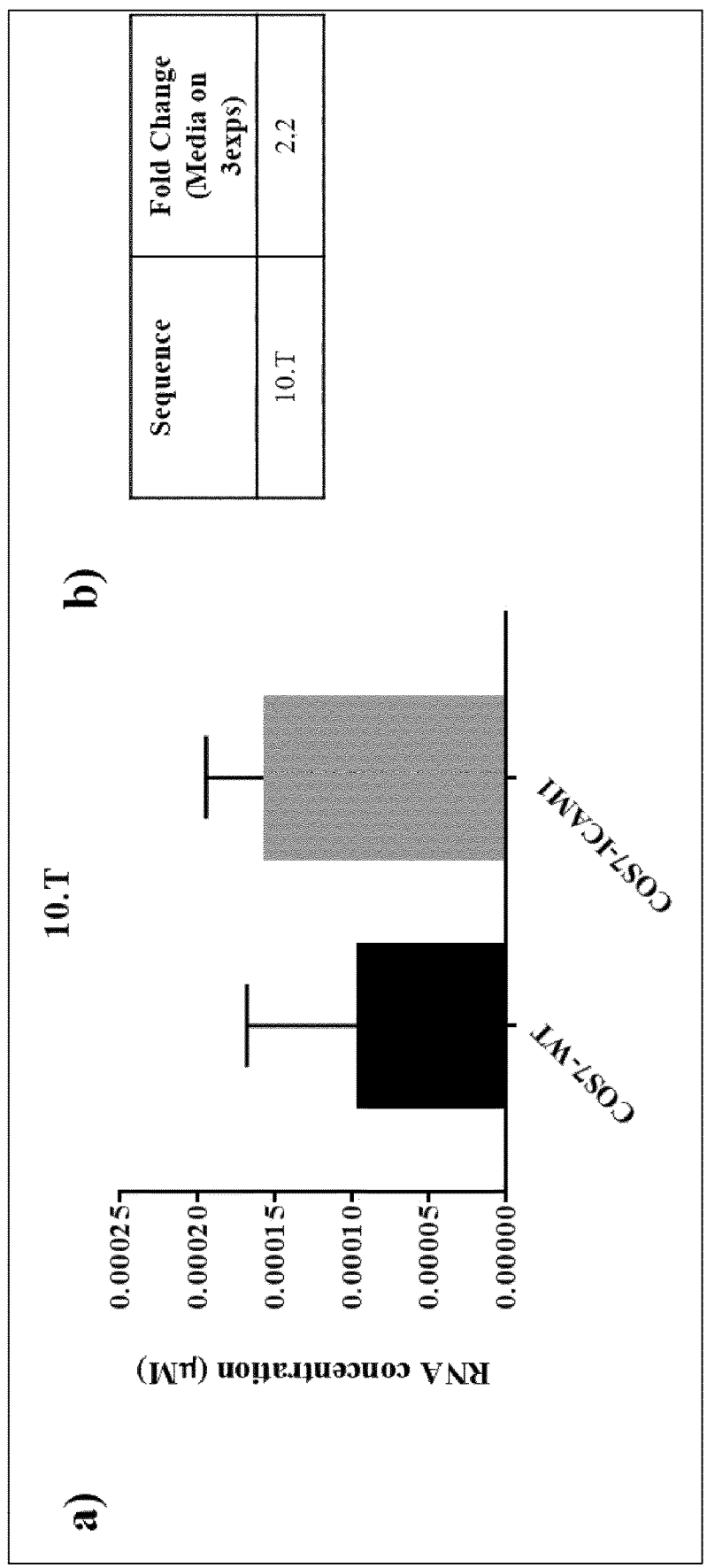
FIG. 5. RT-qPCR binding assay for the 10.T sequence selected by anti-ICAM-1 cell-SELEX. a) RT-qPCR for the 10.T sequence selected to perform experimental triplicates; b) summary table of experimental triplicate fold ratio. Each bar shows the mean±standard deviation values from three experiments.

The RNA sequence 10.T was incubated at 50 nM, as final concentration, for 15 minutes at 37° C. on COS7-WT and COS7-ICAM-1. The ratio comparing binding values of COS7-ICAM-1 over COS7-WT (fold change) is reported in FIG. 5, showing a value of 2.2. This result confirmed the ability of the aptamer 10.T (SEQ ID NO: 1), as well as of the original molecule 12c-10 (SEQ ID NO: 2), to bind the target ICAM-1 in its physiological conformation exposed on the membrane of the cell surface.

EXAMPLE 3

Binding Assay of Aptamer 10.T to COS7-ICAM-1

Figure 7:
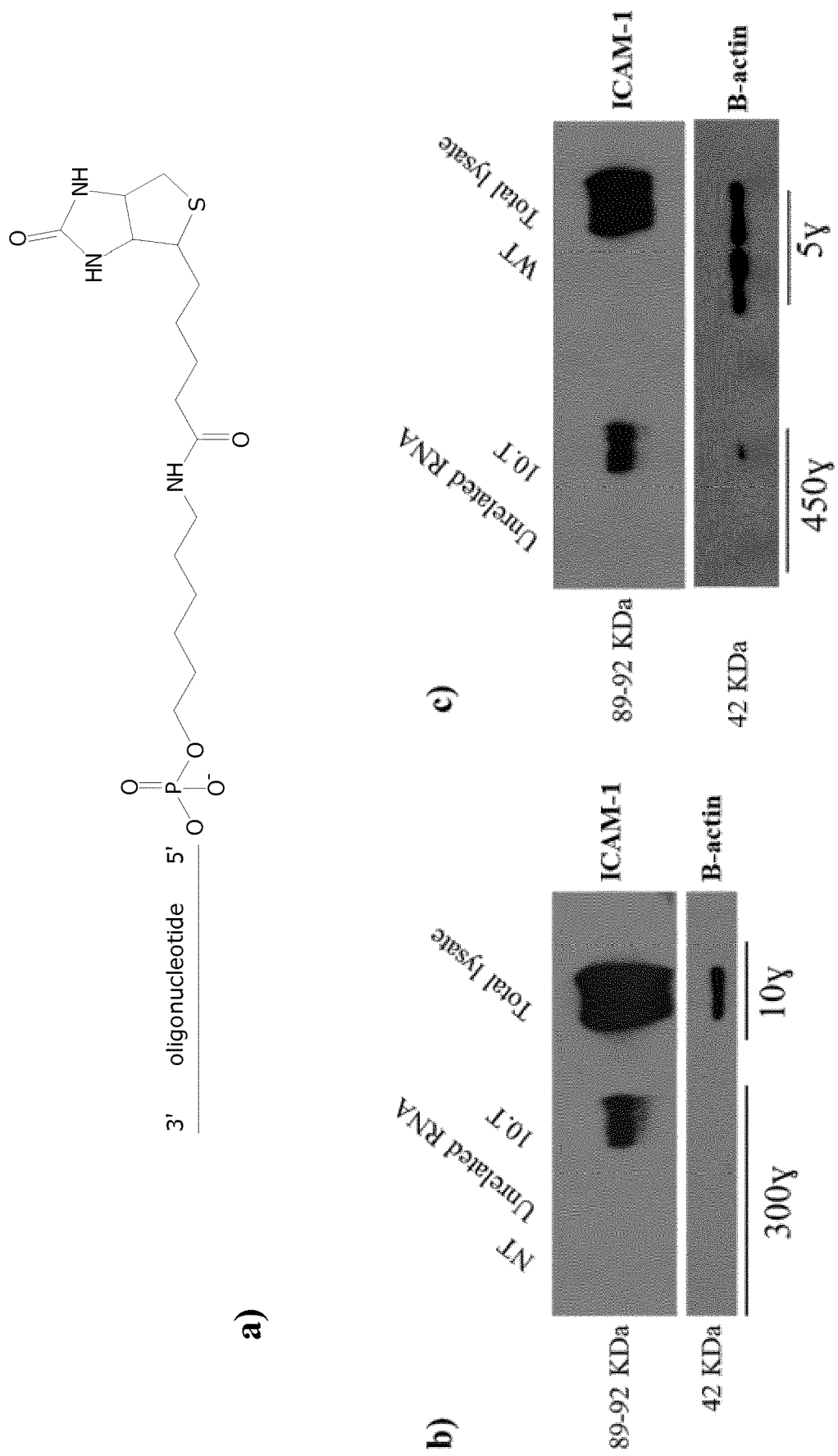
FIG. 7. 10.T sequence pull-down assay. a) Structure of oligonucleotides biotinylated at 5'-end; b) 300 μg or c) 450 μg of COS7, transiently transfected with ICAM-1 cDNA, lysate were incubated with 1 μM of biotinylated 10.T sequence and an ICAM-1-unrelated 2'F-RNA sequence used as negative control.

The binding of aptamer 10.T was further investigated in a different experiment. A pull-down assay with aptamer 10.T biotinylated at 5'-end was performed to verify that the sequence bound its target, ICAM-1. COS7 cells transiently transfected with ICAM-1 cDNA for 48 h were collected and 300 µg of lysate were incubated with 1 µM of biotinylated aptamer 10.T and an ICAM-1-unrelated 2'F-RNA sequence used as negative control. The complexes were successively incubated with Streptavidin Agarose beads. After several washings and denaturation, samples were analyzed by immunoblotting, as shown in FIG. 7.

Results indicated that 10.T binds ICAM-1, whereas the ICAM-1-unrelated 2'F-RNA sequence and an untreated sample gave no signal after hybridization with anti-ICAM-1 antibody. This experiment was performed in duplicate.

EXAMPLE 4

Aptamer 10.T Stability in Human Serum

Figure 6:
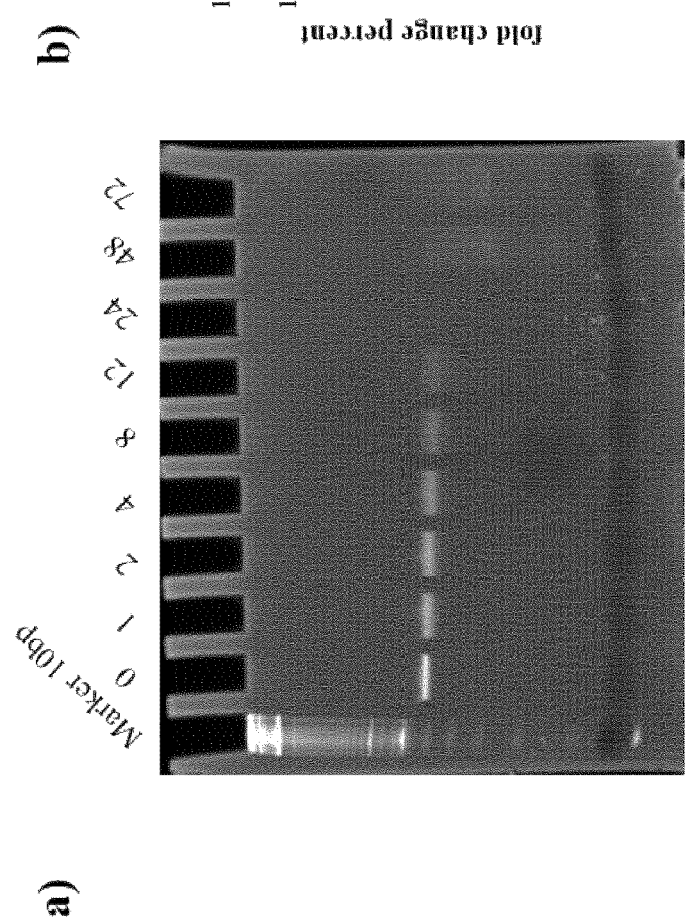
FIG. 6. 10.T sequence stability in human serum. a) 10.T sequence samples collected at different times were loaded on a denaturing gel and b) bands were quantified by ImageJ program.

Aptamer 10.T was tested for stability in human serum. It was incubated in 87% human serum at 37° C. The samples were collected at different times (T0, 1, 2, 4, 8, 12, 24, 48, 72 h), incubated with proteinase K for 1 h at 37° C. in order to degrade serum proteins and loaded on a denaturing gel. Results showed an half-life for aptamer 10.T between 4 and 8 h. Stability results are shown in FIG. 6.

EXAMPLE 5

Conjugation of a Fluorophore to the 5'-End of Aptamer 10.T

To demonstrate the potential use of aptamer 10.T in imaging applications, the RNA sequence was conjugated at its 5'-end to the commercial dye Alexa Fluor 488 after insertion of a $C_{12}$-amino linker (5'-$C_{12}$-$NH_2$). The amino linker was inserted at the 5'-terminal phosphate by condensation with a $C_{12}$ aliphatic diamine in basic catalysis. The resulting free $NH_2$ moiety was coupled with the commercially available Alexa Fluor 488-NHS ester, to form a covalent amide bond. The Alexa Fluor 488-NHS ester was dissolved in high-quality anhydrous dimethylformamide (DMF) or dimethylsulfoxide (DMSO), and the reaction was carried out in 0.1-0.2 M sodium bicarbonate buffer, pH 8.3, at room temperature. Purification was performed by PAGE followed by HPLC.

EXAMPLE 6

Affinity Assays of Aptamer 10.T and its Conjugate Thereof

Figure 8:
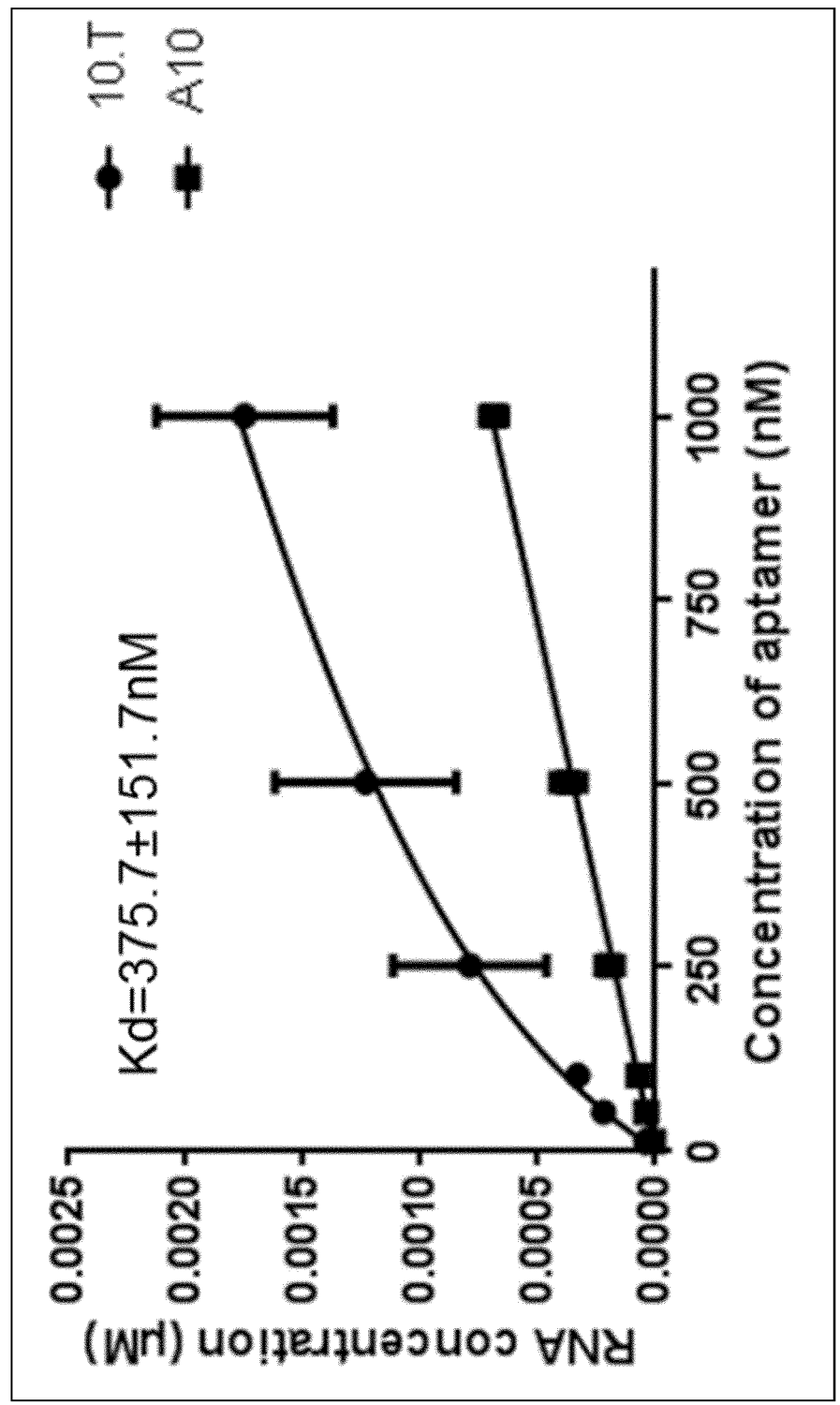
FIG. 8. Determination of binding affinity of 10.T sequence to COS7-ICAM-1 by RT-qPCR binding assay. The recovered RNA (μM) of varying concentrations of 10.T sequence and the unrelated sequence A10 were plotted to determine dissociation constant $K_d$ by using GraphPad software. The experiment was repeated three times and the error bars represent the standard deviation of means.

In order to investigate the affinity to the target, the aptamer 10.T was incubated on COS7-ICAM-1 cells at increasing concentrations (10-50-100-250-500-1000 nM) for 15 minutes at 37° C. after pre-treatment with yeast tRNA 200 µg/mL. The same experiment was carried out with the unrelated aptamer A10, as negative control (sequence disclosed in Lupold S. E. et al., Cancer Res. 2002, 62, 4029-4033). The binding was evaluated by RT-qPCR. As can be seen from FIG. 8, the $K_d$ value resulted 375.7±151.7 nM.

Figure 9:
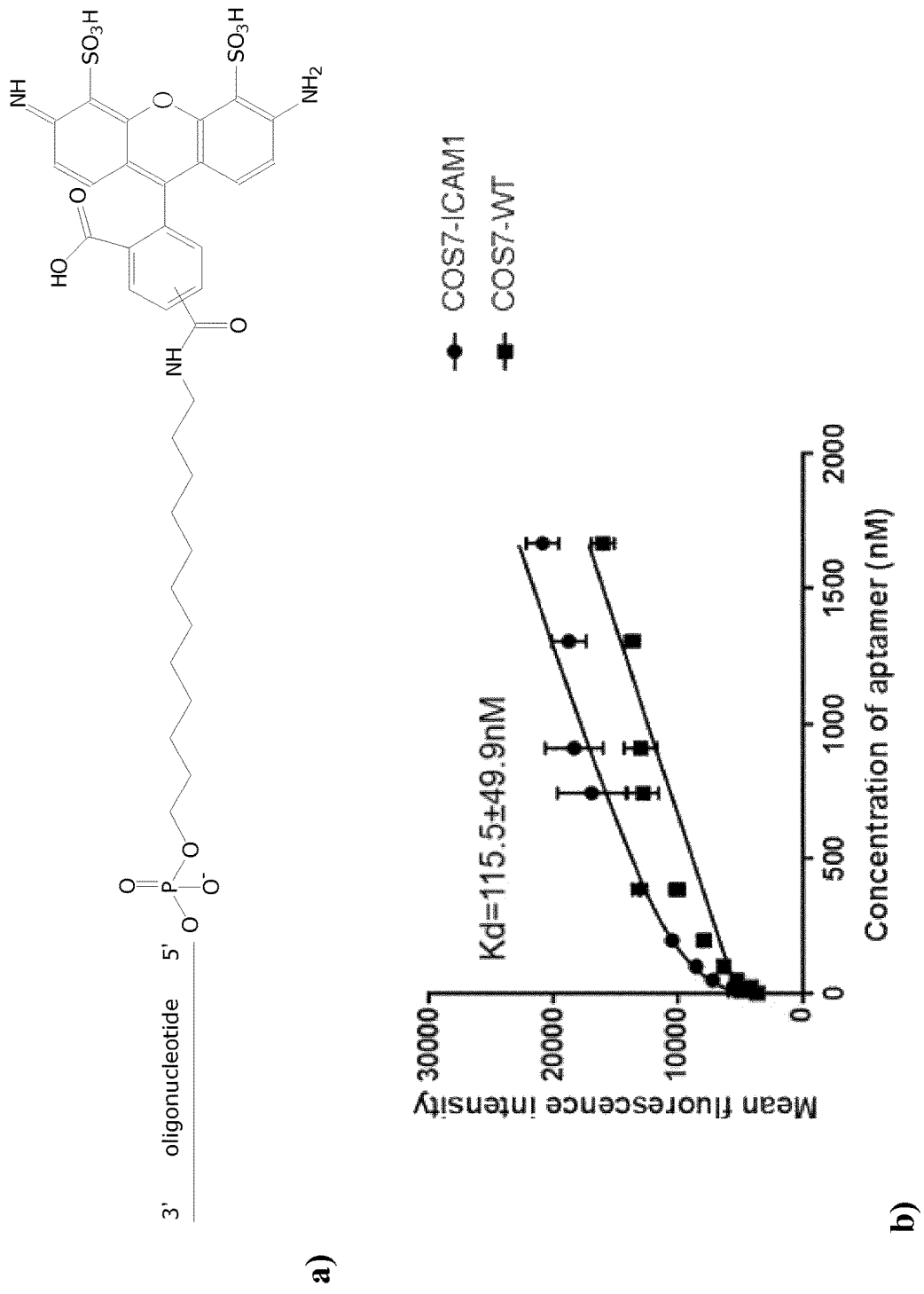
FIG. 9. Determination of binding affinity of Alexa488-10.T conjugate to COS7-WT and COS7-ICAM-1 by flow cytometry. a) Structure of 10.T sequence conjugated to Alexa-488 fluorophore at the 5'-end by a C12 amino linker. b) The mean fluorescence intensity of varying concentration of Alexa488-10.T conjugate obtained was plotted to determine dissociation constant $K_d$ by using GraphPad software. The experiment was repeated six times and error bars represent the standard deviation of means.

To confirm or deeply investigate aptamer 10.T $K_d$ value by using another technique, the conjugate of aptamer 10.T with Alexa Fluor-488 obtained in Example 5 was incubated on COS7-WT and COS7-ICAM-1 at increasing concentrations (10-50-100-200-400-800-1000-1500-2000 nM) at 37° C. for 30 minutes, after pre-treatment with yeast tRNA 200 µg/mL. The experiment was analyzed by flow cytometry and performed 6 times, giving a $K_d$ of 115.5±49.9 nM as a result (see the results in FIG. 9).

Figure 10:
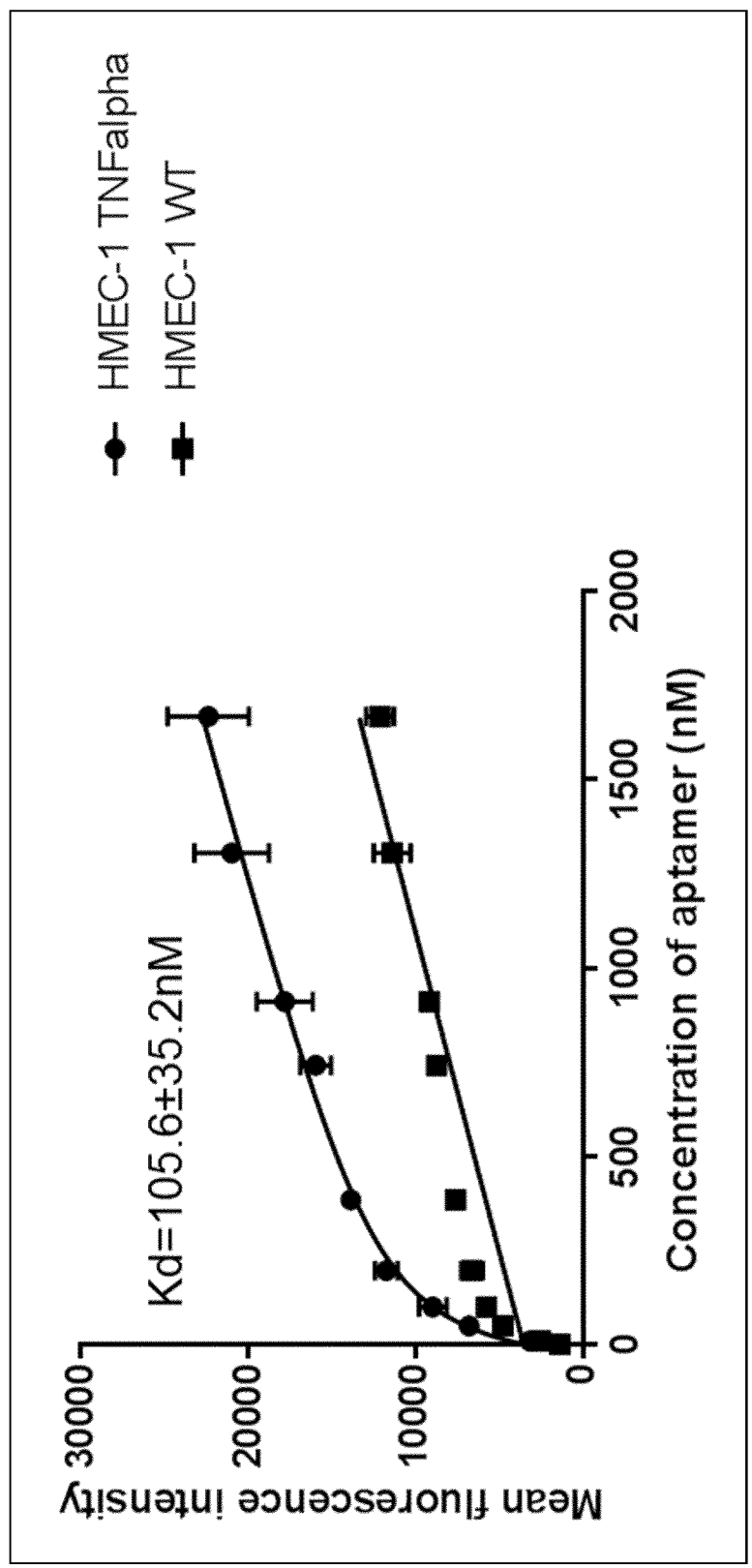
FIG. 10. Determination of binding affinity of Alexa488-10.T conjugate to HMEC1-WT and HMEC1-TNFalpha by flow cytometry. The mean fluorescence intensity of varying concentration of Alexa488-10.T conjugate obtained was plotted to determine dissociation constant $K_d$ by using GraphPad software. The experiment was repeated three times and error bars represent the standard deviation of means.

A comparable result was obtained on induced HMEC-1 cell line. HMEC-1 cells were stimulated with TNFalpha for 48h to induce ICAM-1 expression. The experiment was performed in the same conditions used for COS7 cells, in triplicate, giving a $K_d$ of 105.6±35.2 nM (see the results in FIG. 10).

EXAMPLE 7

ELONA Assay (Binding Affinity to HSA)

Figure 11:
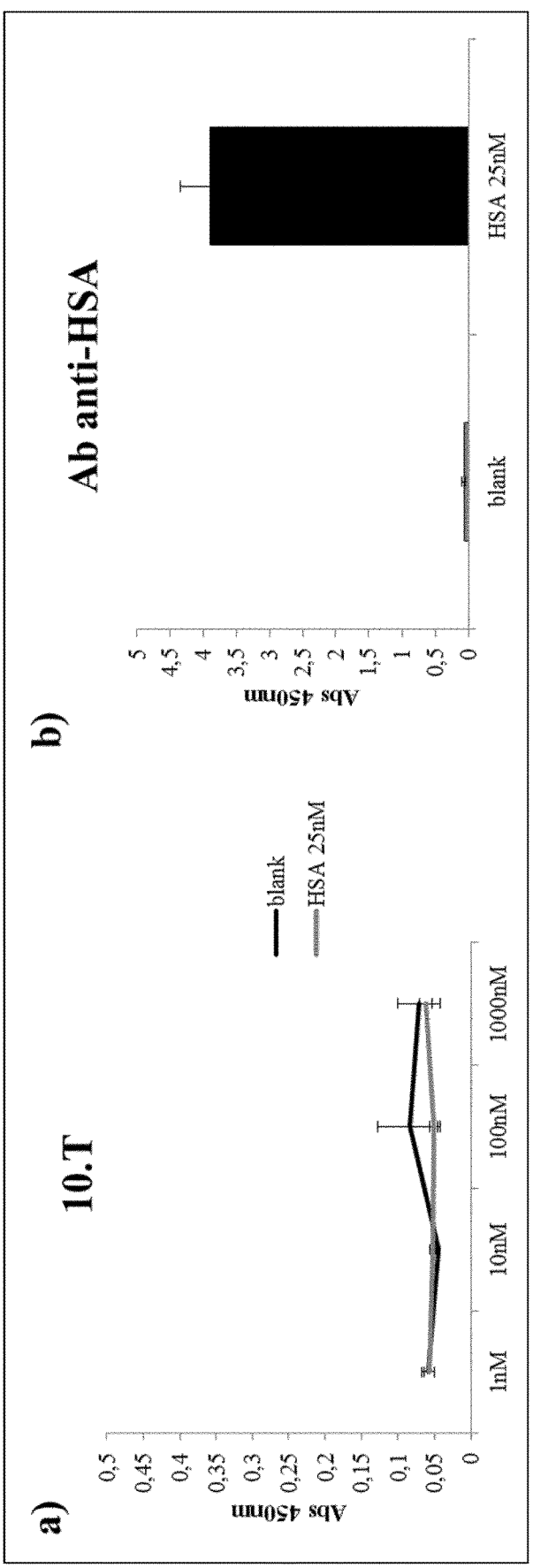
FIG. 11. 10.T sequence $K_d$ evaluation for HSA by ELONA assay. Absorbance at 450 nm for 10.T sequence (a) and polyclonal antibody anti-HSA (b).

The ELONA assay was performed to calculate a $K_d$ value for human serum albumin (HSA). Biotinylated aptamer 10.T was incubated at increasing concentrations (1-10-100-1000 nM) on 96 well microtiter high binding plates previously coated or not-coated with HSA 25 nM. It was not possible to calculate $K_d$ value, indicating that 10.T does not react with HSA up to 1000 nM. For each experiment a biotinylated polyclonal antibody anti-HSA was used as positive control. The results of this experiment are reported in FIG. 11.

The invention claimed is:

1. An aptamer that binds to Intercellular Adhesion Molecule-1 (ICAM-1), comprising the RNA sequence SEQ ID NO: 1.

2. The aptamer of claim 1, characterized in that it has a length of up to 100 nucleotides.

3. The aptamer of claim 1, which is able to bind to ICAM-1 with a dissociation constant falling within a range from 500 nM to 50 nM.

4. The aptamer of claim 1, comprising the RNA sequence SEQ ID NO: 2.

5. The aptamer of claim 1, wherein all the pyrimidine residues are modified to 2'-fluoropyrimidines.

6. The aptamer of claim 5, which is further modified to comprise at least one chemical modification, wherein said modification is selected from: chemical substitution at a sugar position; chemical substitution at a phosphate position; and a chemical substitution at a base position of the nucleic acid.

7. The aptamer of claim 6, wherein the modification is selected from the group consisting of incorporation of a modified nucleotide, conjugation to a compound, and labeling with a reporter moiety.

8. The aptamer of claim 7, wherein the reporter moiety is selected from the group consisting of a fluorophore moiety, a magnetic or paramagnetic moiety, a radiolabel moiety, an affinity label, an X-ray moiety, an ultrasound imaging moiety, a photoacoustic imaging moiety and a nanoparticle-based moiety.

9. A method of treating a ICAM1-related state, disorder, dysfunction, condition or disease comprising administering an aptamer according to claim 1 to a subject in need thereof.

10. The method according to claim 9, wherein said ICAM-1-related state, disorder, dysfunction, condition or disease is inflammation or an inflammation-associated disease.

11. A method of imaging comprising administering an aptamer according to claim 1 to a subject and imaging a body tissue or organ system expressing ICAM-1.

12. The method according to claim 11, wherein said tissue or organ system are endothelium or blood vessels, respectively.

13. A diagnostic, therapeutic or imaging composition comprising an aptamer as defined in claim 1, with at least one pharmaceutically acceptable carrier, excipient, or a combination thereof.

14. A method according to claim 11, wherein said imaging is based on magnetic resonance imaging, positron-emission tomography (PET), computed tomography (CT), ultrasound, photoacoustic imaging (PAI), near-infrared fluorescence (NIRF) or single photon emission computed tomography (SPECT).

* * * * *

SEQUENCE LISTING

```
<160> NUMBER OF SEQ ID NOS: 2

<210> SEQ ID NO 1
<211> LENGTH: 55
<212> TYPE: RNA
<213> ORGANISM: Artificial Sequence
<220> FEATURE:
<223> OTHER INFORMATION: synthetic aptamer

<400> SEQUENCE: 1
ucaugauacg uugcgugagc aacugcggcg cuaaaguuug guugacuagu acaug         55

<210> SEQ ID NO 2
<211> LENGTH: 84
<212> TYPE: RNA
<213> ORGANISM: Artificial Sequence
<220> FEATURE:
<223> OTHER INFORMATION: synthetic aptamer

<400> SEQUENCE: 2
gggaagagaa ggacauauga ucaugauacg uugcgugagc aacugcggcg cuaaaguuug   60
guugacuagu acaugaccac uuga                                          84
```